United States Patent [19]
Okutsu et al.

[11] Patent Number: 5,696,071
[45] Date of Patent: Dec. 9, 1997

[54] TRIS (3-AMINOPROPYL)AMINE DERIVATIVE AND DETERGENT COMPOSITION CONTAINING THE SAME

[75] Inventors: Akiko Okutsu, Sakai; Tomohito Kitsuki, Wakayama; Katsumi Kita, Izumisano, all of Japan

[73] Assignee: Kao Corporation, Tokyo, Japan

[21] Appl. No.: 750,982

[22] PCT Filed: Jun. 21, 1995

[86] PCT No.: PCT/JP95/01246

§ 371 Date: Jan. 7, 1997

§ 102(e) Date: Jan. 7, 1997

[87] PCT Pub. No.: WO96/01800

PCT Pub. Date: Jan. 25, 1996

[30] Foreign Application Priority Data

Jul. 8, 1994 [JP] Japan ................................ 6/157555

[51] Int. Cl.$^6$ .................... C11D 1/06; C11D 1/40; C11D 1/62

[52] U.S. Cl. ................ 510/126; 510/127; 510/128; 510/478; 510/479; 510/480; 510/495; 510/501; 510/504; 510/506; 510/130; 510/237; 510/502; 510/357; 510/137; 562/102; 562/106; 562/565; 564/153; 564/154; 564/197; 564/512

[58] Field of Search ................... 510/126, 127, 510/156, 428, 477, 489, 490, 494, 495, 501, 504, 505, 128, 478, 479, 480; 562/30, 102, 103, 104, 105, 106, 107, 109, 110, 561, 564, 565, 571, 594, 595, 598; 564/152, 153, 154, 160, 197, 201, 511, 512

[56] References Cited

FOREIGN PATENT DOCUMENTS 1-321434  12/1989  Japan.

*Primary Examiner*—Ardith Hertzog
*Assistant Examiner*—John R. Hardee
*Attorney, Agent, or Firm*—Oblon, Spivak, McClelland, Maier & Neustadt, P.C.

[57] ABSTRACT

Described are a tris(3-aminopropyl)amine derivative represented by the following formula (1):

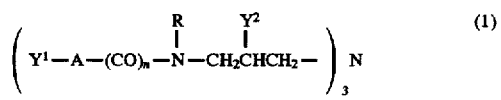

wherein R represents a $C_{1-24}$ alkyl or alkenyl group which may have —OH, A represents a $C_{1-6}$ alkylene or alkenylene group which may have —OH, —COOH or —SO$_3$H, Y$^1$ represents —COOH, —SO$_3$H or —OSO$_3$H, Y$^2$ represents —OH, —OSO$_3$H or —OCO—A—COOH and n stands for 0 or 1, or a salt or quaternized product thereof; and a detergent composition containing the same. The compound according to the present invention has low skin or hair irritation, has excellent foaming power and imparts favorable touch feeling to the skin or the like.

9 Claims, No Drawings

TRIS (3-AMINOPROPYL)AMINE DERIVATIVE AND DETERGENT COMPOSITION CONTAINING THE SAME

TECHNICAL FIELD

The present invention relates to tris(3-aminopropyl)amine derivatives, salts and quaternized products thereof, and intermediates therefor, which are useful as bases for hair or skin cosmetic compositions, detergents, emulsifiers, conditioning agents or the like.

BACKGROUND ART

As detergents, surfactants such as alkyl sulfates, polyoxyethylene alkylsulfates and alkylbenzene sulfonates have conventionally been used. Many of these surfactants are however accompanied with the drawback that their skin irritation is slightly strong upon practical use. In consideration of such a problem, surfactants having weak skin irritation, for example, alkylphosphates and acylated amino acid salts have come to be used as a base or emulsifier for a hair or skin cosmetic composition, a detergent for skin, or the like. Furthermore, reflecting the diversified demand of users and their inclination to higher-grade products, there has recently been a request for the surfactants which have, in addition to less skin irritation, advantages such as good foaming power, capability of imparting good touch feeling to the skin, and the like. However, there has so far been no surfactants which can satisfy such requests.

Accordingly, an object of the present invention is to provide a compound which has less skin irritation, is excellent in foaming power, can impart the skin or the like with favourable touch feeling and is therefore useful as a base for hair or skin cosmetic compositions, detergents, emulsifiers or conditioning agents.

DISCLOSURE OF THE INVENTION

With forgoing in view, the present inventors have conducted an extensive investigation. As a result, it has been found that a novel compound represented by the formula (1), which will be described below, has low skin irritation, imparts the skin or the like with favourable touch feeling, and has excellent foaming power. It has also been found that the incorporation of the above compound makes it possible to provide a detergent having excellent detergency and foaming power and is free from skin irritation, leading to the completion of the invention.

The present invention therefore provides a tris(3-aminopropyl)amine derivative represented by the following formula (1):

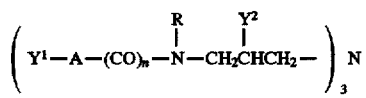  (1)

wherein R represents a linear or branched $C_{1-24}$ alkyl or alkenyl group which may be substituted by a hydroxyl group, A represents a linear or branched $C_{1-6}$ alkylene or alkenylene group which may be substituted by a hydroxyl group, a carboxyl group or a sulfonic acid group, $Y^1$ represents a carboxyl group, a sulfonic acid group or a sulfuric acid residue; $Y^2$ represents a hydroxyl group, a sulfuric acid residue or a group —OCO—A—COOH; and n stands for 0 or 1; a salt and quaternized product of the derivative; and an intermediate for the derivative.

The present invention also provides a detergent composition comprising the above tris(3-aminopropyl)amine derivative (1), or a salt or quaternized product of the derivative.

BEST MODES FOR CARRYING OUT THE INVENTION

As compounds each having a structure close to that of the compound of the present invention, compounds having a 2-hydroxypropanediamine structure (described in U.S. Pat. No. 3,654,158, German Patent No. 3607884, U.S. Pat. No. 4,982,000, Japanese Patent Laid-Open No. Hei 1-233264, Japanese Patent Laid-Open No. Hei 2-223515 and the like) are known. However, these compounds have a diamine structure and do not contain an anionic functional group such as carboxyl group, sulfonic acid group or sulfuric acid residue so that they are largely different from the compound of the present invention in its structure and function.

R in the above formula (1) represents a linear or branched $C_{1-24}$ alkyl or alkenyl group which may be substituted by a hydroxyl group and as the specific examples of it, the following groups can be given.

Examples of the linear alkyl group include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl and tetracosyl groups. Exemplary branched alkyl groups include methylhexyl, ethylhexyl, methylheptyl, ethylheptyl, methylnonyl, methylundecyl, methylheptadecyl, hexyldecyl and octyldecyl groups.

Illustrative of the linear alkenyl group include ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl, henicosenyl, docosenyl, tricosenyl and tetracosenyl. Examples of the branched alkenyl group include methylhexenyl, ethylhexenyl, methylheptenyl, ethylheptenyl, methylnonenyl, methylundecenyl, methylheptadecenyl, hexyldecenyl and octyldecenyl groups.

There is no particular limitation to be imposed on the substituting position of the hydroxyl group in the linear or branched alkyl or alkenyl group substituted by a hydroxyl group. Examples of such an alkyl or alkenyl group include the above-exemplified alkyl or alkenyl groups which have been, at any position, substituted by a hydroxyl group.

Of these, linear or branched $C_{6-24}$ alkyl or alkenyl groups are preferred as R, with linear or branched $C_{6-12}$ alkyl groups being more preferred and with linear $C_{6-10}$ alkyl groups being particularly preferred.

A in the above formula (1) represents a linear or branched $C_{1-6}$ alkylene or alkenylene group which may be substituted by a hydroxyl group, carboxyl or sulfonic acid group and as the specific examples of it, following groups can be given.

Examples of the alkylene or alkenylene groups include methylene, ethylene, trimethylene, tetramethylene, pentamethylene, hexamethylene, methylethylene, ethylethylene, ethenylene, propenylene, butenylene, pentenylene and hexenylene groups. Of these, groups having 1–4 carbon atoms are preferred, with those having 1–3 carbon atoms being more preferred and with methylene, ethylene, trimethylene and ethenylene groups being particularly preferred.

The above-exemplified alkylene or alkenylene group can be substituted by a hydroxyl group (—OH), sulfonic acid group (—$SO_3H$) or carboxyl group (—COOH). The substitution is effected by using these substituents either singly or in combination, and 1–4 substituents in total. Preferred examples of the hydroxy-substituted alkylene or alkenylene group include 1,2-dihydroxyethylene, 1-hydroxyethylene, 2-hydroxyethylene and 2-hydroxytrimethylene groups. Preferred examples of the sulfonic-acid-substituted alkylene or alkenylene group include 1-sulfoethylene and 2-sulfoethylene groups. As the carboxyl-substituted alkylene or alkenylene group, 1-carboxyethylene and 2-carboxyethylene groups are particularly preferred.

As the hydroxy- and carboxy-substituted alkylene or alkenylene group, a 2-carboxy-2-hydroxytrimethylene group is particularly preferred. As hydroxy- and sulfonic-acid-substituted alkylene or alkenylene group, 1-hydroxy-2-sulfoethylene and 2-hydroxy-1-sulfoethylene groups are particularly preferred.

Since the compound (1) according to the present invention contains a sulfonic acid group (—SO₃H), a sulfuric acid residue (—OSO₃H) or a carboxyl group (—COOH), it can form salts with various basic substances. Examples of the salt include alkali metal salts, alkaline earth metal salts, amine salts, basic amino acid salts and ammonium salts. Specific examples include salts with sodium, potassium, lithium, magnesium, calcium, trimethylamine, triethylamine, tributylamine, monoethanolamine, diethanolamine, triethanolamine, lysine, arginine, choline or ammonia. Of these, alkali metal salts are preferred, with sodium salts being particularly preferred.

Incidentally, the compound (1) according to the present invention contains a tertiary amino group so that when n stands for 0 in the formula (1), there are some cases where the compound takes a quaternary salt structure in which a proton is positioned on the nitrogen atom of the tertiary amino group and this amino tertiary group serves as an ammonium cation, while the sulfonic acid group, sulfuric acid residue or carboxyl group serves as a sulfonic acid anion, sulfuric acid anion or carboxyl anion.

The compound (1) according to the present invention can be quaternized as needed. Specific examples of the quaternized compound include compounds wherein all or some of four nitrogen atoms in the formula (1) have been quaternized. Examples of the group which can be linked onto the nitrogen atom for said quaternization include $C_{1-6}$ alkyl groups, a benzyl group and groups represented by —(R⁷O)ₘH (wherein R⁷ represents a C₂ alkylene group and m stands for 1–50) each of which may be substituted by a hydroxyl, carboxyl or sulfonic acid group. Here, the examples of the $C_{1-6}$ alkyl groups which may be substituted by a hydroxyl, carboxyl or sulfonic acid group include methyl, ethyl, propyl, isopropyl, butyl, pentyl, hexyl, hydroxyethyl, 1,2-dihydroxypropyl, carboxymethyl, carboxypropyl and 3-sulfo-2-hydroxypropyl groups. Specific examples of the group represented by —(R⁷O)ₘH include polyoxyethylene and polyoxypropylene groups. Of these, those of the above formula wherein m stands for 1–20 are preferred. Incidentally, the quaternized product of the compound (1) of the present invention is able to exist in the case where in the formula (1), n stands for 0.

The compound (1) of the present invention can be prepared, for example, in accordance with any one of the following reactions (a)–(e).

[Reaction a]

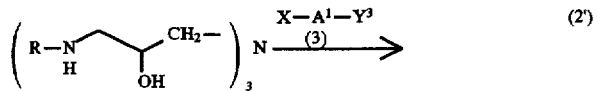

[Reaction a]
-continued

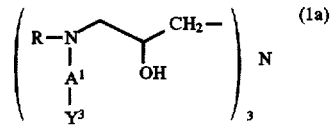

wherein R has the same meaning as defined above, x represents a halogen atom, A¹ represents a $C_{1-6}$ alkylene or alkenylene group which may be substituted by a hydroxyl or carboxyl group; and Y³ represents a sulfonic acid group or a carboxyl group.

Described specifically, the compound (1a) of the present invention can be prepared by reacting a tris(3-amino-2-hydroxypropyl)amine derivative (2') with the compound (3) or a salt thereof.

The reaction between the compound (2)' and the compound (3) is conducted by reacting the compound (3) or a salt thereof in an amount of 3–10 moles per mole of the compound (2)' at 20°–150° C., preferably at 40°–100° C., in the presence of an inert solvent while maintaining the pH at 8–10. Here, the examples of the halogen atom represented by A² in the compound (3) include chlorine, bromine and iodine atoms, with a chlorine atom being more preferred. Specific examples of the compound (3) or a salt thereof include sodium chloroacetate, sodium 3-chloro-2-hydroxypropanesulfonate, sodium 3-chloropropionate and sodium 4-chloro-n-butyrate. Of these, sodium chloroacetate and sodium 3-chloro-2-hydroxypropanesulfonate are more preferred. Examples of the inert solvent usable here include water and polar solvents such as methanol, ethanol, isopropyl alcohol, dimethylformamide and dimethylsulfoxide. These solvents can be used either singly or in combination, but it is preferred to use water, a lower alcohol or a mixed solvent of water and a lower alcohol. When in the above reaction, the compound (3) is added in an excessive amount to the compound (2)', prepared is the compound of the present invention in which all or some of the nitrogen atoms in the formula (1) have been quaternized.

There are some cases where the reaction mixture after the completion of the above reaction contains, in addition to the target compound of the present invention (1a), inorganic salt, unreacted compound (2)', compound (2)' to which one or two moles of the compound (3) have been added and unreacted compound (3). In such a case, the reaction mixture can be purified by the following method except for the case where the reaction mixture can be used as is. For purification, a conventional method such as solvent fractionation, ion exchange chromatography, recrystallization or electrodialysis can be employed. The target compound so obtained may be isolated as a free base or may be isolated in the form of a desired salt by salt exchange in accordance with an ordinary means such as neutralization with a desired basic substance. Examples of the basic substance usable here include sodium hydroxide, potassium hydroxide, lithium hydroxide, magnesium hydroxide, calcium hydroxide, ammonia, trimethylamine, triethylamine, tributylamine, alkanolamine (monoethanolamine, diethanolamine, triethanolamine and the like), lysine, arginine and choline. Of these, hydroxides of an alkali metal such as sodium hydroxide and potassium hydroxide are preferred.

[Reaction b]

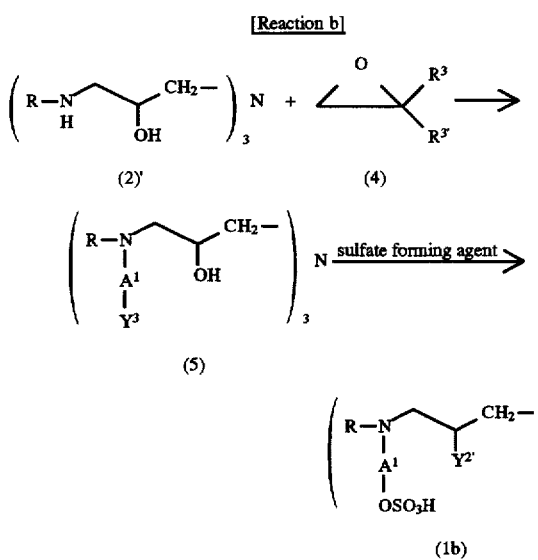

wherein R, A¹ and Y² have the same meanings as defined above; $R^3$ and $R^{3'}$ are the same or different and each independently represents a hydrogen atom, or an alkyl or alkenyl group which may be substituted by a hydroxyl or carboxyl group; and $Y^{2'}$ represents a hydroxyl group or a sulfuric acid residue.

Described specifically, the compound of the present invention (1b) can be prepared by reacting a tris(3-amino-2-hydroxypropyl)amine derivative (2)' with an epoxy compound (4), reacting the resulting compound (5) with a sulfate forming agent and optionally neutralizing the reaction mixture with a basic substance.

It is preferred that the reaction between the compound (2)' and the epoxy compound (4) is conducted, for example, in an inert solvent, preferably at 100°–200° C., notably 130°–180° C. and at this time, the compound (4) is reacted in an amount of 3–7 moles relative to the compound (2)'. No particular limitation is imposed on the inert solvent employed in the above reaction insofar as it is an aprotic solvent. In consideration of the cost and solubility, solvents such as lower hydrocarbons, aromatic hydrocarbons, ethyl ethers and halohydrocarbons are preferred. In addition, it is preferred that the above reaction is conducted in a pressure container such as autoclave in consideration of the boiling points of the epoxy compound (4) and inert solvent employed. As the epoxy compound (4), ethylene oxide, propylene oxide and butylene oxide are preferred because of a low cost, with ethylene oxide being particularly preferred.

In the next step, it is preferred to conduct the reaction of the compound (5) so obtained with a sulfate forming agent such as $ClSO_3H$, $SO_3$ or the like within a temperature range of from −75° C. to 150° C. in an inert solvent or solventless manner. Relative to the compound (5), $ClSO_3H$ or $SO_3$ is preferably added in an amount of 3–8 moles. In the neutralizing reaction optionally conducted after the completion of this reaction, basic substances similar to those described in [Reaction a] can be employed.

Incidentally, in the first stage of the above reaction b, a reaction mixture which has reacted only at one or two sites, among three reaction sites, happens to be by-produced. The resulting reaction mixture can be used as is, but if higher purity is required, the reaction mixture can be purified by a usual means, for example, recrystallization, column chromatography or distillation. In the second stage of the reaction, a reaction mixture which has reacted at all or some of the reaction sites, among 6 sites, is prepared, depending on the using amount of $ClSO_3H$ or $SO_3$. The reaction mixture so obtained can be used as is for various applications. For the applications where higher purity is required, the reaction mixture can be used after fractionation and purification as needed in a manner similar to the above.

[Reaction c]

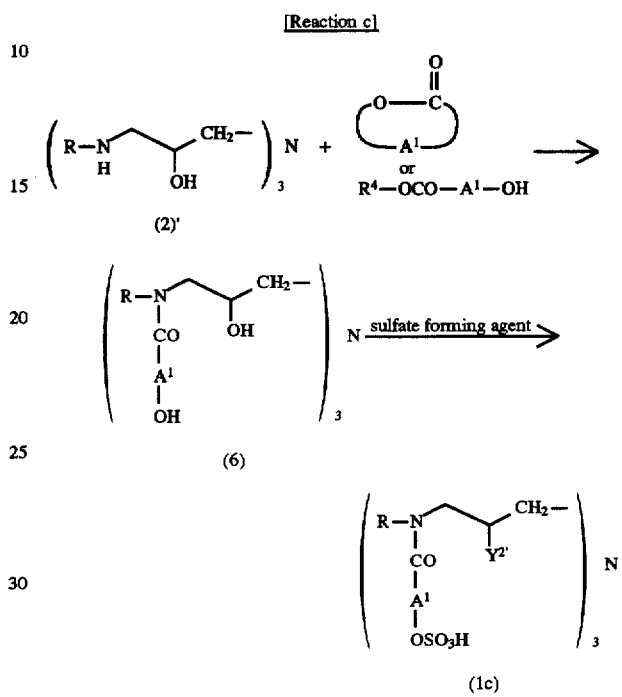

wherein R, A¹ and $Y^{2'}$ have the same meanings as defined above and $R^4$ represents a hydrogen atom or an alkyl group which may contain a substituent.

Described specifically, the compound (1c) of the present invention is prepared by reacting the compound (2)' with a lactone or a hydroxycarboxylic acid, reacting the resulting amide alcohol (6) with a sulfate forming agent and optionally neutralizing the reaction mixture with a basic substance.

It is preferred that the reaction between the compound (2)' and the lactone or hydroxycarboxylic acid is conducted, for example, in an inert solvent or solventless manner, preferably at 20°–180° C., notably 40°–150° C. and at this time, the lactone or hydroxycarboxylic acid is reacted in an amount of 3–7 moles relative to the compound (2)'. No particular limitation is imposed on the inert solvent usable in the above reaction insofar as it is an aprotic solvent. In consideration of the cost and solubility, however, solvents such as lower hydrocarbons, aromatic hydrocarbons, ethyl ethers and halohydrocarbons are preferred. As the lactones and oxycarboxylic acids usable in the above reaction, γ-lactone, δ-lactone, glycolic acid, lactic acid and α-hydroxy acid, and methyl esters and ethyl esters thereof are preferred because of the low cost.

It is preferred that the reaction between the amide alcohol (6) so obtained and the sulfate forming agent such as $ClSO_3H$ or $SO_3$ is conducted in an inert solvent or solventless manner at the temperature range of from −75° C. to 150° C. and at this time, $ClSO_3H$ or $SO_3$ is used in an amount of 3–8 moles relative to the amide alcohol (6). The neutralization reaction conducted as needed after the completion of the above reaction can be carried out in a similar manner to that in the above reaction a or b.

Incidentally, in the first stage of the above reaction c, a reaction mixture which has reacted only at one or two sites, among three reaction sites, happen to be by-produced. The resulting reaction mixture can be used as is, but for the applications where higher purity is required, the reaction mixture can be purified by a usual means, for example, recrystallization, column chromatography or distillation. In the second stage of the reaction, a reaction mixture which has reacted at all or some of the reaction sites, among 6 sites, is prepared, depending on the using amount of $ClSO_3H$ or $SO_3$. The reaction mixture so obtained can be used as is for various applications. For the applications where higher purity is required, the reaction mixture can be used after fractionation and purification as needed in a manner similar to the above.

[Reaction d]

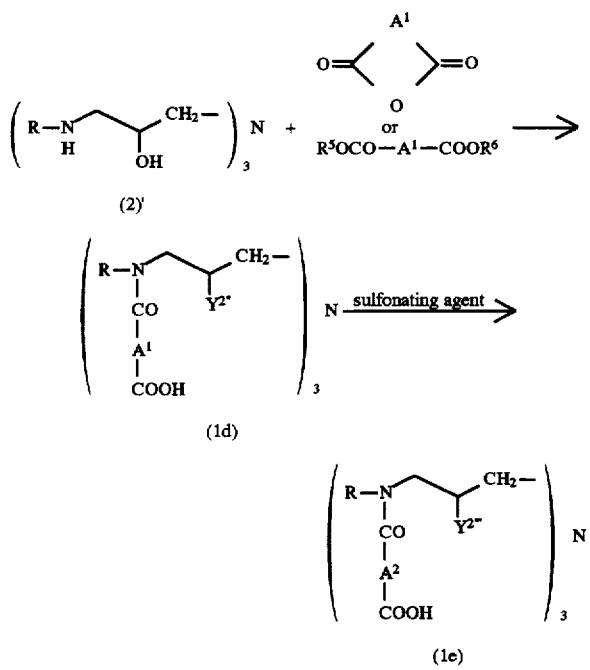

wherein R and $A^1$ have the same meanings as defined above, $R^5$ and $R^6$ each represents a hydrogen atom or an alkyl or alkenyl group which may have a substituent, $A^2$ represents a linear or branched $C_{1-6}$ alkylene group which may be substituted by a hydroxyl or carboxyl group and has been substituted by a sulfonic acid group, $Y^{2''}$ represents a hydroxyl group or a group —OCO—$A^1$—COOH and $Y^{2'''}$ represents a hydroxyl group or a group —OCO—$A^2$OOH.

The compound of the present invention (1d) or salt thereof can be prepared by reacting the compound (2)' with an acid anhydride, or a dicarboxylic acid or ester thereof, hydrolyzing the ester portion of the reaction mixture in the case where the ester is employed, and neutralizing the reaction mixture or hydrolyzate with a basic substance as needed. When the compound (1d) so obtained contains a group —CH=CH— in $A^1$, the compound (1e) of the present invention can be prepared by reacting the compound (1d) with a sulfonating agent such as $SO_3$, sodium sulfite or $NaHSO_3$ and neutralizing the reaction mixture with a basic substance as needed.

It is preferred that the reaction between the compound (2)' and the acid anhydride is conducted, for example, in the presence of an anhydrous inert solvent, at 20°–150° C., preferably at 40°–100° C. and at this time, the acid anhydride is reacted preferably in an amount of 3–8 moles relative to the compound (2)'. Examples of the anhydrous inert solvent usable in the above reaction include ethyl ether, tetrahydrofuran, benzene and pyridine. In the above reaction, depending on the excessive amount of the acid anhydride, all or some of the three hydroxyl groups at the 2-position react with the acid anhydride and can be converted to the group —OCO—$A^1$—COOH.

It is preferred that the reaction between the compound (2)' and a dicarboxylic acid or ester thereof is conducted, for example, in an inert solvent, at 40°–180° C., preferably at 80°–150° C. and at this time, the dicarboxylic acid or ester thereof is reacted in an amount of 3–6 moles relative to the compound (2)'. This reaction is preferably conducted while removing the resultant alcohol or water from the reaction mixture. Examples of the inert solvent usable in the above reaction include hexane, benzene, toluene and xylene.

Incidentally, the examples of the alkyl or alkenyl group represented by $R^5$ or $R^6$ in the dicarboxylate ester include those having 1–5 carbon atoms. Of these, methyl and ethyl groups are particularly preferred.

Incidentally, when a dicarboxylate ester is used here, an intermediate represented by the formula (7) can be obtained and it becomes necessary to hydrolyze the intermediate so obtained, for example, in a water-containing alcohol in the presence of an acid or basic catalyst.

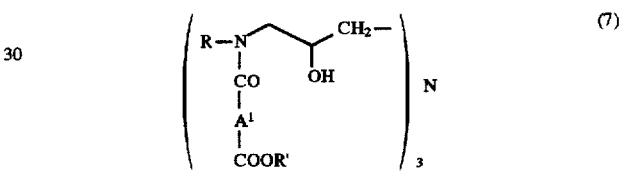

wherein R and $A^1$ have the same meanings as defined above and R' represents an alkyl or alkenyl group corresponding to $R^5$ or $R^6$.

It is preferred that the reaction between the compound (1d) having a group —CH=CH— in $A^1$ and a sulfonating agent such as $SO_3$, sodium sulfite or sodium bisulfate is conducted, for example, in water at 30°–100° C., preferably 40°–80° C., at pH 4.0–11.0, preferably 5.0–8.0, and at this time, $SO_3$, and sodium sulfite or sodium bisulfate is reacted in an amount of 1–8 moles, preferably 1–3 moles relative to the —CH=CH— group in the compound (1d).

The compounds (1d) and (1e) of the present invention can be prepared by the neutralization reaction in a similar manner to that employed for each of the above reactions a–c. Upon neutralization reaction, a compound in which only one or two amino groups have been amidated, or a compound in which only one or two hydroxyl groups have been esterified are by-produced, however, the reaction mixture can be used for various applications as is. If a compound having a higher purity is required, the reaction mixture can be fractionated and purified by a conventional method, for example, recrystallization, column chromatography, electrodialysis or the like.

[Reaction e]

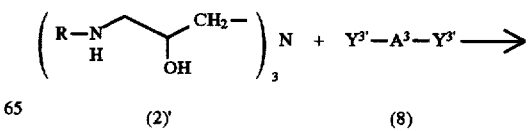

-continued
[Reaction e]

$$\left( \begin{array}{c} R-N \\ | \\ A^4 \\ | \\ Y^3 \end{array} \begin{array}{c} CH_2- \\ | \\ OH \end{array} \right)_3 N$$

(1f)

wherein R and $Y^3$ have the same meanings as defined above, $A^3$ represents a $C_{1-6}$ alkenylene group which may be substituted by a hydroxyl or carboxyl group, $A^4$ represents a $C_{1-6}$ alkylene group which may be substituted by a hydroxyl or carboxyl group, $Y^{3'}$ s are the same or different and each independently represents a hydrogen atom, a carboxyl group, a sulfonic acid group or an alkoxycarbonyl group with the proviso that two $Y^{3'}$ s do not represent a hydrogen atom at the same time.

Described specifically, the invention compound (1f) or salt thereof can be prepared by reacting the compound (2)' with an olefin compound (8), hydrolyzing the ester portion of the reaction mixture when the ester is used as the compound (8), and then neutralizing the reaction mixture or the hydrolyzate with a basic substance as needed. It is preferred that the reaction between the compound (2)' and the olefin compound (8) is conducted, for example, in the presence of an inert solvent at 20°–80° C., preferably from room temperature to 60° C. and at this time, the compound (8) is reacted in an amount of 3–6 moles relative to the compound (2)'. Examples of the inert solvent usable here include methanol, ethanol, isopropyl alcohol, ethyl ether, tetrahydrofuran, benzene and pyridine. In particular, pyridine is preferably used when a carboxylic acid is employed as the olefin compound (8). Incidentally, when an ester is employed as the olefin compound (8), it becomes necessary to hydrolyze the ester portion of the resulting compound, for example, in a water-containing alcohol in the presence of an acid or basic catalyst.

When n stands for 0 in the formula (1), the reaction of the compound (1) with a quaternizing agent makes it possible to prepare the compound (1) in which all or some of its four nitrogen atoms have been quaternized, for example, a compound represented by the following formula (1)'.

$$\left( \begin{array}{c} R \quad Y_2 \\ | \oplus \quad | \\ Y^1-A-N-CH_2CHCH_2- \\ | \\ Z \end{array} \right)_3 N$$

wherein R, A, $Y^1$ and $Y^2$ have the same meanings as defined above and Z represents a $C_{1-6}$ alkyl or alkenyl group which may be substituted by a sulfonic acid group, carboxyl group or hydroxyl group, a benzyl group or a group —$(R^7O)_m H$ ($R^7$ and m have the same meanings as defined above).

Examples of the quaternizing agent include $C_{1-6}$ alkyl halides which may be substituted by a hydroxyl group, carboxyl group or sulfonic acid group, benzyl halides and alkylene oxides, and salts thereof. Of these, alkyl halides are more preferred. Examples of the above alkyl group include methyl, ethyl, n-propyl, n-butyl and isopropyl groups. Exemplary halogen atoms include chlorine, bromine and iodine. Of these, methyl chloride is particularly preferred.

The tris(3-amino-2-hydroxypropyl)amine derivative (2)' used as a raw material for the compound (1) of the present invention in the above reactions a–e can be prepared, for example, in accordance with the following reaction scheme:

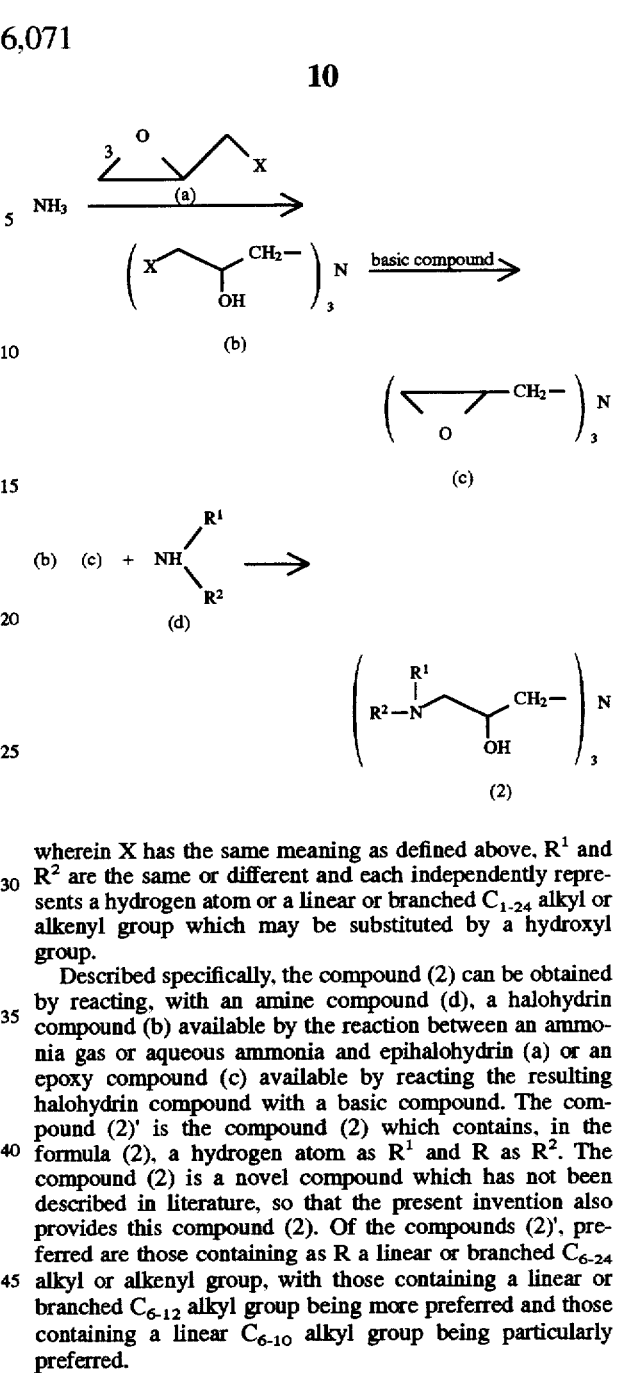

wherein X has the same meaning as defined above, $R^1$ and $R^2$ are the same or different and each independently represents a hydrogen atom or a linear or branched $C_{1-24}$ alkyl or alkenyl group which may be substituted by a hydroxyl group.

Described specifically, the compound (2) can be obtained by reacting, with an amine compound (d), a halohydrin compound (b) available by the reaction between an ammonia gas or aqueous ammonia and epihalohydrin (a) or an epoxy compound (c) available by reacting the resulting halohydrin compound with a basic compound. The compound (2)' is the compound (2) which contains, in the formula (2), a hydrogen atom as $R^1$ and R as $R^2$. The compound (2) is a novel compound which has not been described in literature, so that the present invention also provides this compound (2). Of the compounds (2)', preferred are those containing as R a linear or branched $C_{6-24}$ alkyl or alkenyl group, with those containing a linear or branched $C_{6-12}$ alkyl group being more preferred and those containing a linear $C_{6-10}$ alkyl group being particularly preferred.

In the above preparation process, examples of the halogen atom represented by X in the epihalohydrin (a) used for the synthesis of the halohydrin compound (b) include chlorine, bromine and iodine, with chlorine being preferred. The reaction between ammonia and the epihalohydrin (a) is conducted, for example, in a solventless manner or in a solvent inert to the reaction such as a lower alcohol, ethyl ether or aromatic hydrocarbon or a mixture thereof, preferably at –20° C. to 100° C., notably at 0° C. to 50° C. When aqueous ammonia is used, the reaction is preferably conducted at 0°–50° C. in a solventless manner or in the solvent of a lower alcohol. The amount ratio of ammonia to epihalohydrin (a) can be determined as needed but the epihalohydrin (a) is preferably used in an amount of 3–6 moles relative to ammonia.

As the basic compound used for the subsequent synthesis of the epoxy compound (c), hydroxides of an alkali metal, carbonates of an alkali metal and amines are preferred, with sodium hydroxide and potassium hydroxide being particularly preferred. The reaction between the halohydrin compound (b) and the basic compound is conducted, for example, in a solvent inert to the reaction such as water or a lower alcohol or a mixture thereof preferably at 0°–80° C., notably 20°–60° C. The amount ratio of the halohydrin compound (b) to the basic compound can be determined as needed but the basic compound is preferably used in an amount of 2–5 moles relative to the halohydrin compound (b).

The reaction between the halohydrin compound (b) or epoxy compound (c) so obtained and the amine compound (d) is conducted, for example, in a solventless manner or in a solvent inert to the reaction of a lower alcohol, ethyl ether or aromatic hydrocarbon or a mixture thereof, preferably at 40°–150° C., notably 60°–100° C. The amount ratio of the compounds used for the reaction can be determined as needed but generally, it is preferred to use the amine compound (d) in an amount of 3–20 moles, particularly 3–10 moles relative to the halohydrin compound (b) or epoxy compound (c).

Of the compounds (2) so obtained, the compound (2)' wherein in the formula (2), $R^1$ represents a hydrogen atom and $R^2$ represents R as described above is useful as a raw material for the invention compound in the reactions a–d. The compound represented by the formula (2) wherein $R^1$ and $R^2$ do not represent a hydrogen atom at the same time is also useful as a raw material, because the reaction of it with the compound (3) permits single-stage preparation of the invention compound (1a)' which has been quaternized.

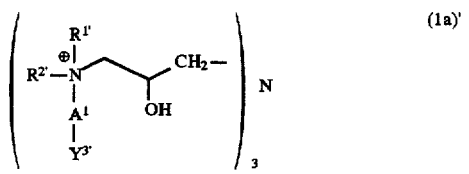

(1a)' wherein $A^1$ and $Y^3$ have the same meanings as defined above and $R^{1'}$ and $R^{2'}$ each represents an alkyl or alkenyl group corresponding to R and $R^2$, respectively.

Incidentally, the compound (2) is excellent in metal corrosion inhibition so that it is useful as an additive component for fuel oils or an additive for lubricating oils for gasoline engine or diesel engine. It can inhibit metal corrosion without lowering the performance of the engine oil or the like. For the use as a metal corrosion inhibitor, the compound (2) of the present invention preferably contains, in the formula (2), a hydrogen atom or a linear or branched, hydroxyl-containing $C_{1-3}$ alkyl group as $R^1$. A compound which contains as $R^1$ a hydrogen atom and as $R^2$ a linear or branched $C_{4-16}$ alkyl group is more preferred, with a compound which contains as $R^1$ a hydrogen atom and as $R^2$ a linear $C_{6-12}$ alkyl group being particularly preferred.

The tris(3-aminopropyl)amine derivative of the present invention represented by the formula (1) has excellent detergency and foaming power so that it can be used for the applications making use of such properties, for example, various detergents such as skin or hair detergent, dishwashing detergent and laundry detergent. In such a case, there is no particular limitation is imposed on the amount of the invention compound (1). Depending on its application, it can be added in an amount ranging from 0.1 to 80 wt. %, preferably 1–50 wt. %.

To the detergent composition according to the present invention, it is possible to add, as needed, various additives known to date such as surfactant, humectant, sterilizer, emulsifier, thickener, pearling agent, divalent metal ion scavenger, alkalizing agent, inorganic salt, resoiling preventive, enzyme, scavenger of available chlorine, reducing agent, bleaching agent, fluorescent dye, solubilizing agent, perfume, caking inhibitor, enzyme activator, antioxidant, antiseptic, colorant, blueing agent, bleach activator, enzyme stabilizer, phase regulator and penetrant.

Examples of the surfactant usable here include anionic surfactant, nonionic surfactant, amphoteric surfactant and cationic surfactant. The anionic surfactant is generally added to improve the detergency, foaming power and feeling upon use. Examples of the anionic surfactant include higher fatty acid salts, alkyl sulfates, alkyl ether sulfates, alkyl sulfonates, α-olefin sulfonates, alkylbenzene sulfonates, alkanoyl isethionates, alkyl succinates, alkyl sulfosuccinates, N-alkanoyl sarcosinates, alkyl phosphates, alkyl ether phosphates and alkyl ether carboxylates. These anionic surfactants each contains an alkyl or acyl group having generally 8–20 carbon atoms and they may be unsaturated. Each of the alkyl ether sulfates, alkyl ether phosphates and alkyl ether carboxylates can contain 1–10 ethylene oxide or propylene oxide units per molecule, with those containing 2–3 ethylene oxide units per molecule being preferred. Examples of the salt of such anionic surfactant include salts of sodium, magnesium and ammonium and mono-, di and triethanolamine salts.

The nonionic surfactant is added generally for the improvement of detergency and feeling upon use. Examples of the nonionic surfactant include polyoxyalkylene alkyl ethers, polyoxyalkylene phenyl ethers, mono- or dialkyl alkanol amides or alkylene oxide adducts thereof, alkyl polyglycosides and monoglycerides. These nonionic surfactants each contain an alkyl or acyl group having generally 8–20 carbon atoms and they may be unsaturated. Examples of the polyoxyalkylene group include polyoxyethylene and polyoxypropylene and mixture thereof. Its condensation degree is generally 6–30.

Examples of the amphoteric surfactant include long-chain alkyldimethyl carboxymethyl betaine and sulfobetaine, while that of the cationic surfactant include long-chain alkyltrimethyl ammonium salts and di-long-chain alkyldimethyl ammonium salts.

Together with the compound (1) of the present invention, the above-exemplified surfactant may be added to the detergent composition in an amount of 0.5 to 60 wt. % based on the detergent composition. For a powdery detergent composition, it may be added preferably in an amount of 10–45 wt. %, while for a liquid detergent composition, it may be added preferably in an amount of 20–50 wt. %. In the case of a bleaching detergent, it is preferred to add the surfactant generally in an amount of 1–10 wt. %, preferably 1–5 wt. %.

Exemplary humectants include glycerin, ethylene glycol, propylene glycol and 1,3-butylene glycol.

Examples of the thickener include polyacrylic acid, a crosslinked polymer of acrylic acid, a copolymer between acrylic acid and a hydrophobic monomer, a copolymer between a carboxylic-acid-containing monomer and an acrylate, a crosslinked polymer between acrylic acid and an acrylate, ester of ethylene glycol or ester of polyethylene glycol (for example, its fatty acid ester) and heteropolysaccharide rubber.

The pearling agent can be selected from $C_{16-22}$ fatty acids, $C_{16-22}$ esters of a fatty acid and an alcohol or $C_{16-22}$ fatty acid esters containing an element such as an alkylene glycol unit. As a suitable alkylene glycol unit, ethylene glycol and propylene glycol can be given as examples. Polyalkylene glycols can also be used. Examples of the suitable polyalkylene glycol include polyethylene glycol and polypropylene glycol.

Examples of the divalent metal ion scavenger include condensed phosphate salts such as tripolyphosphates, pyrophosphates and orthophosphates; aluminosilicates such as zeolite; synthetic crystalline phyllosilicates; nitrilotriacetates; ethylenediaminetetraacetates; citrates; isocitrates; and polyacetal carboxylates.

The divalent metal ion scavenger may be added in an amount of 0–50 wt. %, preferably 5–40 wt. %. It is more desired to use a phosphorus-free divalent metal ion scavenger.

Examples of the alkalizing agent or inorganic salt include silicates, carbonates, sesquicarbonates, sulfates and alkanol amines. The alkalizing agent or inorganic salt may be added in an amount of 0–80 wt. %.

Examples of the resoiling preventive include polyethylene glycol, polyacrylates, polyacrylic copolymers such as a copolymer between acrylic acid and maleic acid, polyvinyl alcohol, polyvinyl pyrrolidone and carboxymethyl cellulose. Some of these resoiling preventives can also serve as divalent metal ion scavengers. The resoiling preventive may be added in an amount of 0–10 wt. %, preferably 1–5 wt. %.

Examples of the enzyme usable in the present invention include cellulase, α-amylase, pullulanase, lipase, hemcellulase, β-glycosidase, glucose oxidase, cholesterol oxidase and protease.

Examples of the scavenger of available chlorine in tap water include ammonium sulfate, urea, guanidine chloride, guanidine carbonate, guanidine sulfamate, thiourea dioxide, monoethanolamine, diethanolamine, triethanolamine and amino acids typified by glycine and sodium glutamate; proteins such as bovine serum albumin and casein; hydrolyzates of protein; meat extract; and fish meat extract. Exemplary reducing agents include alkali metal salts such as thiosulfates, sulfites and dithionites, alkaline earth metal salts and Rongalit C. Sulfites are particularly preferred, because they stabilize the enzyme in the washing liquid.

Examples of the bleaching agent include percarbonates, perborates, sulfonated zinc phthalocyanates or sulfonate aluminum phthalocyanates, and hydrogen peroxide. For the use as a bleaching detergent, sodium peroxide is particularly effective. The bleaching agent may be added preferably in an amount of 1–95 wt. %, more preferably 5–95 wt. %, and particularly 20–95 wt. %.

As the fluorescent dye, those commonly used for a detergent can be used. For a liquid detergent, a solubilizing agent, for example, a lower alcohol such as ethanol, a lower alkylbenzene sulfonate such as benzene sulfonate or p-toluene sulfonate, or a polyol such as glycerin or propylene glycol can be added.

Each detergent composition according to the present invention can be prepared by using the invention compound (1) and the above known components in combination in a manner known per se in the art. The form of the detergent, for example, liquid, powder, granule or the like can be selected depending on the application purpose.

EXAMPLES

The present invention will hereinafter be described more specifically by examples. It should however be borne in mind that the present invention will not be limited to or by the following examples.

Example 1

In a reaction vessel, 0.93 mole of epichlorohydrin and 100 ml of ethanol were charged. To the resulting mixture, 20.4 ml of 25% aqueous ammonia at room temperature were gently added dropwise. They were reacted for about 3 hours while the temperature was maintained at 45°–50° C. After the removal of excess epichlorohydrin from the reaction mixture, 2.7 moles of octylamine were added to the residue, followed by the reaction at 80°–90° C. for 10 hours. After the completion of the reaction, the excess octylamine was removed and the product obtained as the hydrochloride in the form of crystals was dissolved in xylene. The resulting solution was washed with an aqueous solution of sodium hydroxide, followed by washing with water, whereby 165 g of tris(4-aza-2-hydroxydodecyl)amine were obtained (yield: 96%).

The compound so obtained gave a single peak at gas chromatography (SE-52, 1%, 0.5 m). The following is the $^1$H-NMR of the compound.

$^1$H-NMR (CDCl$_3$): δ (ppm) 0.9 (9H, triplet, a) 1.3 (30H, wide singlet, b) 1.5 (6H, wide singlet, c) 2.4–2.7 (18H, complex multiplet, d,e,g) 3.8 (3H, quintet, f)

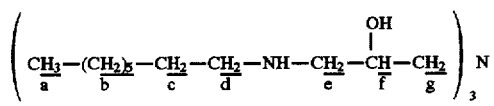

Example 2

In a reaction vessel, 0.93 mole of epichlorohydrin and 100 ml of ethanol were charged, followed by the addition of 20.4 ml of 25% aqueous ammonia at room temperature. They were reacted for about 3 hours while the temperature was kept at 45°–50° C. After the removal of the excess epichlorohydrin from the reaction mixture, 2.7 moles of hexylamine were added to the residue, followed by reaction at 80°–90° C. for about 8 hours. After the completion of the reaction, the excess hexylamine was removed and the product obtained as a hydrochloride in the form of crystals was dissolved in xylene. The resulting solution was washed with an aqueous solution of sodium hydroxide, followed by washing with water, whereby 126 g of tris (4-aza-2-hydroxydecyl)amine were obtained (yield: 86%).

The compound so obtained gave a single peak (RT=15.5 min) as a result of gas chromatography (SE-52, 1%, 0.5 m). The following is the $^1$H-NMR of the compound. $^1$H-NMR (CDCl$_3$): δ (ppm) 0.85 (9H, triplet, a) 1.3 (18H, wide singlet, b) 1.45 (6H, quintet, c) 2.4–2.8 (18H, complex multiplet, d,e,g) 3.75 (3H, quintet, f)

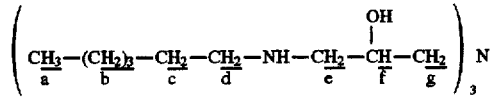

Example 3

In a reaction vessel, 1.35 mole of epichlorohydrin and 100 ml of ethanol were charged, followed by the dropwise addition of 20.4 ml of 25% aqueous ammonia at room temperature. They were reacted for about 3 hours while the temperature was kept at 45°–50° C. After the removal of the excess epichlorohydrin from the reaction mixture, 2.7 moles of 2-(ethylamino)ethanol were added to the residue, followed by reaction at 80°–90° C. for about 5 hours. After the completion of the reaction, the excess 2-(ethylamino) ethanol was removed and the product obtained as a hydrochloride in the form of crystals was dissolved in xylene. The resulting solution was washed with an aqueous solution of sodium hydroxide, followed by washing with water, whereby 122 g of tris(4-aza-4-ethyl-2, 6-dihydroxy) amine were obtained (yield: 90%).

The compound so obtained gave a single peak as a result of gas chromatography (SE-52, 1%, 0.5 m). The following is the $^1$H-NMR of the compound. $_1$H-NMR (CDCl$_3$): δ (ppm) 1.0 (9H, triplet, c) 2.4–2.7 (24H, complex multiplet, b,d,e,g) 3.4 (6H, triplet, a) 3.7 (3H, quintet, f)

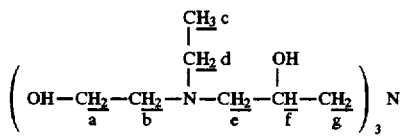

Example 4

In a reaction vessel, 28.6 g (0.05 mole) of tris(4-aza-2-hydroxydodecyl)amine and 50 ml of ethanol were charged. After heating to 70° C., a 40% aqueous solution of 17.5 g (0.15 mole) of sodium chloroacetate was added dropwise to the resulting solution. The resulting mixture was reacted at 70° C. for 19 hours while the pH was adjusted to 9–10 with an aqueous solution of sodium hydroxide. During the reaction, 23.3 g (0.2 mole) of sodium chloroacetate were added in several portions.

The reaction mixture was concentrated under reduced pressure. To the residue, n-butanol was added, followed by washing with water. The n-butanol layer was brought into dryness, whereby 31.8 g of tris(4-aza-2-hydroxy-4-carboxymethyldodecyl)amine were obtained (yield: 85%).

As a result of mass analysis (FAB ionization method) of the compound so obtained, it showed a peak of m/z=747 (M+H). $^1$H-NMR (CDCl$_3$): δ (ppm) 0.94 (9H, triplet, a) 1.36 (30H, wide singlet, b) 1.49 (6H, wide singlet, c) 2.35–2.75 (18H, complex multiplet, d,e,g) 3.18 (6H, wide singlet, h) 3.83 (3H, quintet, f)

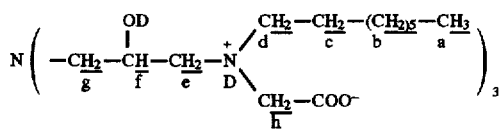

The compound had low skin irritation and excellent foaming power and it imparted the skin and hair with favourable touch feeling.

Example 5

In a reaction vessel, 28.6 g (0.05 mole) of tris(4-aza-2-hydroxydodecyl)amine and 50 ml of ethanol were charged, followed by heating to 70° C. To the resulting mixture, an aqueous solution of 32.8 g (0.15 mole) of sodium 3-chloro-2-hydroxypropanesulfonate was added dropwise, followed by the reaction at 70° C. for 20 hours while adjusting the pH at 9–10 with sodium hydroxide. During the reaction, 43.7 g (0.2 mole) of sodium 3-chloro-2-hydroxypropanesulfonate were added in several portions.

The reaction mixture was concentrated under reduced pressure. To the residue, n-butanol was added, followed by washing with water. The n-butanol layer was brought into dryness, whereby 43.5 g of tris(4-aza-2,6-dihydroxy-4-octyl-7-sulfoheptyl)amine were obtained (yield: 88.2%).

As a result of the mass analysis (FAB ionization method) of the compound so obtained, it showed a peak of m/z=987 (M+H). $^1$H-NMR (D$_2$O): δ (ppm) 0.86 (9H, triplet, a) 1.30(30H, wide singlet, b) 1.64(6H, wide singlet, c) 2.50–2.95 (24H, complex multiplet, d,e,g,h) 3.06 (6H, wide singlet, j) 4.00 (3H, quintet, f) 4.35 (3H, quintet, i)

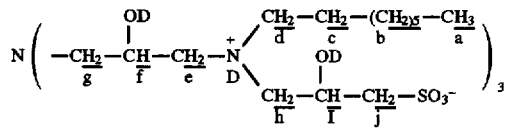

The compound had low skin irritation and excellent foaming power and imparted the skin and hair with favourable touch feeling.

Example 6

In a reaction vessel, 28.6 g (0.05 mole) of tris(4-aza-2-hydroxydodecyl)amine, 15.0 g (0.15 mole) of succinic anhydride and 100 ml of chloroform were charged, followed by reflux for 4 hours. From the reaction mixture, chloroform was distilled off under reduced pressure. To the residue, n-butanol was added, followed by washing with water until the wash liquid stopped showing acidity. The n-butanol layer was brought into dryness, whereby 43 g of tris(4-aza-4-octyl-5-oxy-2-hydroxy-7-hexacarboxy)amine were obtained (yield: 98.6%).

The tris(4-aza-2-hydroxy-4-octyl-5-oxy-2-hydroxy-7-carboxyhexyl)amine so obtained was suspended in water. The resulting suspension was dissolved in an aqueous solution of sodium hydroxide while adjusting the pH to 7 therewith. The resulting solution was lyophilized, whereby a sodium salt of tris(4-aza-2-hydroxy-4-octyl-5-oxy-7-carboxyhexyl)amine was obtained.

As a result of the mass analysis (FAB ionization method) of the acid-type compound which had been obtained by treating the above-obtained salt with 1N hydrochloric acid, it showed a peak of m/z=873 (M+H). 1H-NMR (D$_2$O): δ (ppm) 0.93 (9H, triplet, a) 1.30 (30H, wide singlet, b) 1.59 (6H, wide singlet, c) 2.35–2.95 (30H, complex multiplet, d,e,g,h,i) 4.06 (3H, quintet, f)

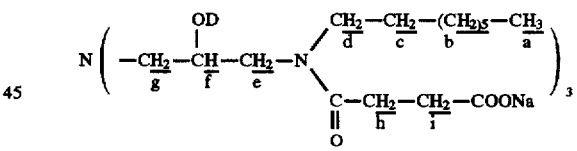

The compound had low skin irritation and excellent foaming power and imparted the skin and hair with favourable touch feeling.

Example 7

In a reaction vessel, 24.4 g (0.05 mole) of tris(4-aza-2-hydroxydecyl)amine, 14.7 g (0.15 mole) of maleic anhydride and 100 ml of ethyl ether were charged, followed by reflux for 6 hours. The reaction mixture was washed with water until the wash liquid stopped showing acidity, followed by removal of the ether layer. The residue so obtained and an aqueous solution of 20.2 g (0.16 mole) of sodium sulfite were mixed and reacted at 60° C. for 4 hours while maintaining the pH at 5–6. After the completion of the reaction mixture, the pH was adjusted to 7 with an aqueous solution of sodium hydroxide. Then, the excess sodium sulfite was removed by electrodialysis.

The residue was then lyophilized, whereby 45.2 g of a sodium salt of tris(4-aza-7-carboxy-4-hexyl-2-hydroxy-5- oxo-7-sulfohexyl)amine were obtained (yield: 85.0%). $^1$H-NMR (D$_2$O): δ (ppm) 0.90 (9H, triplet, a) 1.32 (18H, wide singlet, b) 1.50 (6H, wide singlet, c) 2.25–3.30 (6H, complex multiplet, d,e,g,h,i) 4.02 (3H, quintet, f)

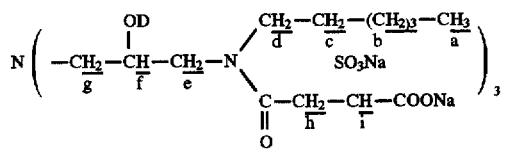

The compound had low skin irritation and excellent foaming power and imparted the skin and hair with favourable touch feeling.

Example 8

In a reaction vessel, 28.6 g (0.05 mole) of tris(4-aza-2-hydroxydodecyl)amine and 21.5 g (0.25 mole) of γ-butyrolactone were charged, followed by heating to 160° C. They were then reacted for 5 hours. After the completion of the reaction, the reaction mixture was purified by column chromatography (silica gel: 500 g, developing solvent: chloroform:methanol=100:1), whereby 34.7 g of tris(4-aza-2,8-dihydroxy-4-octyl-5-oxooctyl)amine were obtained (yield: 83.6%).

In another reaction vessel, 33.2 g (0.04 mole) of tris(4-aza-2,8-dihydroxy-4-octyl-5-oxooctyl)amine which had been obtained above and 150 ml of dichloromethane were charged. To the resulting mixture, a dichloromethane solution of 8 ml (0.12 mole) of chlorosulfuric acid was gently added dropwise under a nitrogen gas stream under ice cooling. The temperature was then gradually returned to the room temperature and hydrochloric acid and dichloromethane produced by the nitrogen gas stream were removed. The residue was poured into water, followed by the adjustment of pH to 7 with an aqueous solution of sodium hydroxide. The solution was desalted by electrodialysis, followed by lyophilization, whereby 44.5 g of a sodium salt of tris(4-aza-2-hydroxy-4-octyl-5-oxo-7-sulfoxyoctyl)amine were obtained (yield: 98%). $^1$H-NMR (D$_2$O): δ (ppm) 0.89 (9H, triplet, a) 1.34 (18H, wide singlet, b) 1.55 (6H, wide singlet, c) 2.55–3.35 (36H, complex multiplet, d,e,g,h,i,f) 3.98 (3H, quintet, f)

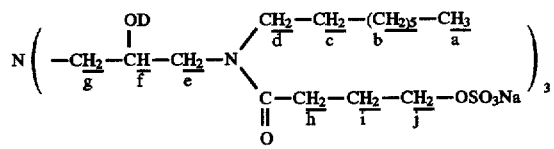

The compound had low skin irritation and excellent foaming power and had imparted the skin and hair with favourable touch feeling.

Example 9

In a reaction vessel, 41.5 g (0.05 mole) of tris(4-aza-2,8-dihydroxy-4-octyl-5-oxooctyl)amine which had been obtained similarly to Example 8 and 150 ml of dichloromethane were charged. To the resulting mixture, a dichloromethane solution of 20 ml (0.3 mole) of chlorosulfuric acid were gently added dropwise under a nitrogen gas stream while ice cooling. The temperature was then gradually returned to the room temperature, followed by removal of hydrochloric acid and dichloromethane produced by the nitrogen gas stream. The residue was poured into water. The resulting mixture was then adjusted to pH 7 with an aqueous solution of sodium hydroxide. The aqueous solution so obtained was desalted by electrodialysis, followed by lyophilization, whereby 71.4 g of a sodium salt of tris(4-aza-4-octyl-5-oxo-2,8-disulfoxyoctyl)amine were obtained (yield: 99%). $^1$H-NMR (D$_2$O): δ (ppm) 0.92 (9H, triplet, a) 1.36 (30H, wide singlet, b) 1.57 (6H, wide singlet, c) 2.45–3.40 (36H, complex multiplet, d,e,g,h,i,f,j) 4.18 (3H, quintet, f)

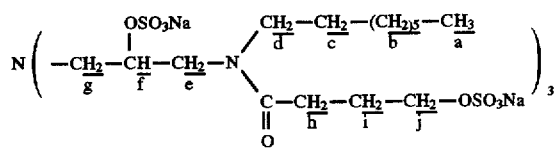

The compound had low skin irritation and excellent foaming power and imparted the skin and hair with favourable touch feeling.

Example 10

In a reaction vessel, 24.4 g (0.05 mole) of tris(4-aza-2-hydroxydecyl)amine, 19 g (0.25 mole) of glycolic acid and 100 ml of xylene were charged. While fractionating the resulting water, reflux was conducted for 15 hours. The excess glycolic acid was removed by washing the reaction mixture with water. The xylene layer was then concentrated under reduced pressure. The residue was decolored and purified by column chromatography (silica gel: 300 g, developing solvent: chloroform:methanol=80:1), whereby 33 g of tris(4-aza-2,6-dihydroxy-4-hexyl-5-oxohexyl)amine were obtained (yield: 99.7%).

In another reaction vessel, 33 g (0.05 mole) of tris(4-aza-2,6-dihydroxy-4-hexyl-5-oxohexyl)amine which had been obtained above and 150 ml of dichloromethane were charged. To the resulting solution, a dichloromethane solution of 10 ml (0.15 mole) of chlorosulfuric acid was gently added dropwise under a nitrogen gas stream under ice cooling. The temperature was then returned gradually to room temperature, followed by removal of hydrochloric acid and dichloromethane which were emitted owing to the nitrogen gas stream. The residue was poured into water. The resulting mixture was adjusted to pH 7 with an aqueous solution of sodium hydroxide. The resulting aqueous solution was desalted by electrodialysis, followed by lyophilization, whereby 47.4 g of a sodium salt of tris(4-aza-2-hydroxy-4-hexyl-5-oxo-6-sulfohexyl)amine were obtained (yield: 98.0%). $^1$H-NMR (D$_2$O): δ (ppm) 0.88 (9H, triplet, a) 1.30 (18H, wide singlet, b) 1.53 (6H, wide singlet, c) 2.50–3.35 (24H, complex multiplet, d,e,g,h) 3.88 (3H, quintet, f)

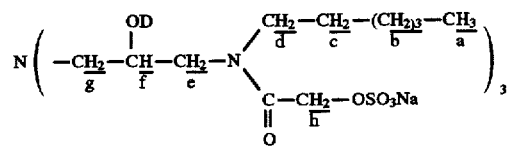

The compound had low skin irritation and excellent foaming power and imparted the skin and hair with favourable touch feeling.

Example 11

In a reaction vessel, 33.1 g (0.05 mole) of tris(4-aza-2,6-dihydroxy-4-hexyl-5-oxohexyl)amine which had been obtained similarly to Example 7 and 150 ml of dichloromethane were charged. To the resulting mixture, a dichloromethane solution of 20 ml (0.3 mole) of chlorosulfuric acid were gently added dropwise under a nitrogen gas stream while ice cooling. The temperature was then gradually returned to the room temperature, followed by removal of the resulting hydrochloric acid and dichloromethane by the nitrogen gas stream.

The residue was poured into water. The resulting mixture was then adjusted to pH 7 with an aqueous solution of sodium hydroxide. The aqueous solution so obtained was desalted by electrodialysis, followed by lyophilization, whereby 61.5 g of a sodium salt of tris(4-aza-4-hexyl-5-oxo-2, 6-disulfoxyhexyl) amine were obtained (yield: 96.5%).

$^1$H-NMR (D$_2$O): δ (ppm) 0.90 (9H, triplet, a) 1.32 (18H, wide singlet, b) 1.55 (6H, wide singlet, c) 2.60–3.35 (24H, complex multiplet, d,e,g,h) 4.00 (3H, quintet, f)

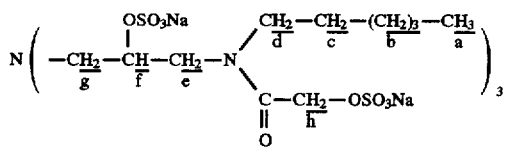

The compound had low skin irritation and excellent foaming power and imparted the skin and hair with favourable touch feeling.

Example 12

In a 1-litre autoclave, 57.2 (0.1 mole) of tris(4-aza-2-hydroxydecyl)amine and 500 ml of xylene were charged. After heating to 155° C., 22 g (0.5 mole) of ethylene oxide were poured into the resulting mixture, followed by reaction for 6 hours while maintaining the temperature at 155° C. After the completion of the reaction, the solvent was distilled off under reduced pressure, whereby 70 g of tris(4-aza-2,6-dihydroxy-4-octylhexyl)amine were obtained (yield: 99%).

In another reaction vessel, 35.2 g (0.05 mole) of tris(4-aza-2,6-dihydroxy-5-octylhexyl)amine which had been obtained above and 150 ml of dichloromethane were charged. To the resulting mixture, a dichloromethane solution of 10 ml (0.15 mole) of chlorosulfuric acid was gently added dropwise under a nitrogen gas stream while ice cooling. Then, the temperature was returned gradually to the room temperature and the resulting hydrochloric acid and dichloromethane were removed by the nitrogen gas stream. The residue was poured into water, followed by the adjustment of pH to 7 with an aqueous solution of sodium hydroxide. The aqueous solution was subjected to desalting treatment by electrodialysis, followed by lyophilization, whereby 50.3 g of a sodium salt of (4-aza-2-hydroxy-4-octyl-6-sulfoxyhexyl)amine were obtained (yield: 99.6%).

$^1$H-NMR (D$_2$O): δ (ppm) 0.91 (9H, triplet, a) 1.35 (30H, wide singlet, b) 1.50 (6H, wide singlet, c) 2.50–3.40 (24H, complex multiplet, d,e,g,h,i) 3.89 (3H, quintet, f)

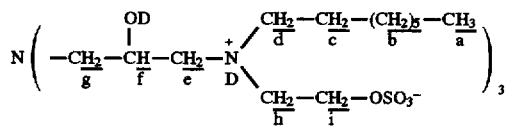

The compound had low skin irritation and excellent foaming power and imparted the skin and hair with favourable touch feeling.

Example 13

In a reaction vessel, 35.2 g (0.05 mole) of tris(4-aza-2,6-dihydroxy-4-octylhexyl)amine which had been obtained similarly to Example 9 and 150 ml of dichloromethane were charged. To the resulting mixture, a dichloromethane solution of 20 ml (0.3 mole) of chlorosulfuric acid were gently added dropwise under a nitrogen gas stream while ice cooling. The temperature was then gradually returned to the room temperature, followed by the removal of the resulting hydrochloric acid and dichloromethane by the nitrogen gas stream.

The residue was then poured into water and the resulting mixture was adjusted to pH 7 with an aqueous solution of sodium hydroxide. The aqueous solution so obtained was subjected to desalting treatment by electrodialysis, followed by lyophilization, whereby 65.5 g of a sodium salt of tris(4-aza-4-octyl-2,6-disulfoxyhexyl)amine were obtained (yield: 99.5%).

$^1$H-NMR (D$_2$O): δ (ppm) 0.89 (9H, triplet, a) 1.30 (30H, wide singlet, b) 1.53 (6H, wide singlet, c) 2.65–3.40 (30H, complex multiplet, d,e,g,h,i) 3.95 (3H, quintet, f)

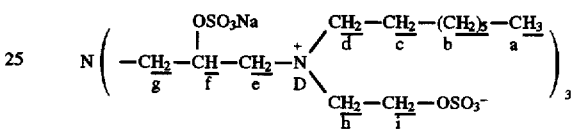

The compound had low skin irritation and excellent foaming power and imparted the skin and hair with favourable touch feeling.

Example 14

In a reaction vessel, 28.6 g (0.05 mole) of tris(4-aza-2-hydroxydodecyl)amine, 17.4 ml (0.16 mole) of ethyl acrylate and 100 ml of ethanol were charged and they were reacted at room temperature for 2 days. The reaction mixture was brought into dryness under reduced pressure. The residue was charged in the reaction vessel and dissolved in a 50 ml 2:1 mixed solvent of ethanol and water. To the resulting solution, 6 g (0.15 mole) of sodium hydroxide were added, followed by stirring at room temperature for 2 hours.

The reaction mixture was concentrated under reduced pressure, followed by the addition of water to prepare an aqueous solution. The aqueous solution so obtained was adjusted to pH 7. The aqueous solution was then subjected to desalting by electrodialysis, followed by lyophilization, whereby 35.6 g of tris(4-aza-2-hydroxy-4-octyl-6-carboxyhexyl)amine were obtained (yield: 90.3%).

$^1$H-NMR (D$_2$O): δ (ppm) 0.91 (9H, triplet, a) 1.33 (30H, wide singlet, b) 1.50 (6H, wide singlet, c) 2.30–3.00 (30H, complex multiplet, d,e,g,h,i) 3.85 (3H, quintet, f)

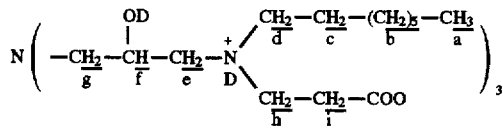

The compound had low skin irritation and excellent foaming power and imparted the skin and hair with favourable touch feeling.

Example 15

In a reaction vessel, 28.6 g (0.05 mole) of tris(4-aza-2-hydroxydodecyl)amine, 20.0 ml (0.16 mole) of dimethyl maleate and 100 ml of ethanol were charged, followed by the reaction at room temperature for 2 hours. The reaction mixture was brought into dryness under reduced pressure.

To another reaction vessel, the residue so obtained was charged and dissolved in a 50 ml 2:1 mixed solvent of ethanol and water. Sodium hydroxide (12 g, 0.3 mole) was added to the resulting solution, followed by stirring at room temperature for 2 hours. The reaction mixture was concentrated under reduced pressure. Water was added to the concentrate to prepare an aqueous solution, which was adjusted to pH 7. The aqueous solution so adjusted was subjected to desalting treatment by electrodialysis, followed by lyophilization, whereby 47.2 g of a sodium salt of tris(4-aza-2-hydroxy-4-octyl-5,6-dicarboxyhexyl)amine were obtained (yield: 92.3%).

$^1$H-NMR (D$_2$O): δ (ppm) 0.93 (9H, triplet, a) 1.35 (30H, wide singlet, b) 1.53 (6H, wide singlet, c) 2.35–3.20 (24H, complex multiplet, d,e,g,i) 3.45 (3H, complex multiplet, h) 3.90 (3H, quintet, f)

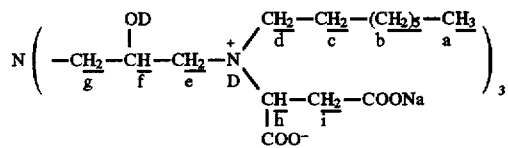

The compound had low skin irritation and excellent foaming power and imparted the skin and hair with favourable touch feeling.

Preparation Example 1

The shampoo having the composition as described below was prepared using the compound of the present invention.

| (Composition) | (wt. %) |
| --- | --- |
| Compound of Example 4 | 15.0 |
| Lauroyl diethanolamide | 3.0 |
| Lauryl dimethylamine oxide | 0.5 |
| Hydroxyethyl cellulose (product of Daicel Chemical Industries, Ltd.) | 0.1 |
| Sodium benzoate | 0.3 |
| Colorant | q.s |
| Perfume | q.s |
| Citric acid | q.s |
| Water | Balance |
| Total | 100.0 |

Preparation Example 2

In a similar manner to Preparation Example 1 except that the compound of Example 4 was replaced by the compounds of Examples 5–15, the shampoos were prepared, respectively.

The shampoos obtained in Preparation Examples 1 and 2 each had excellent foaming power and detergency and had good touch feeling at the time of hair washing or rinsing.

Preparation Example 3

The body shampoo having the composition as described below was prepared using the compound of the present invention.

| (Composition) | (wt. %) |
| --- | --- |
| Compound of Example 5 | 17.0 |
| Polyoxyethylene (EO = 3) lauryl glycoside | 5.0 |
| Lauryl dimethylamine oxide | 3.0 |
| Glycerin | 4.0 |
| Sucrose fatty acid ester | 1.0 |
| Methyl paraben | 0.3 |
| Colorant | q.s. |
| Perfume | q.s. |
| Citric acid | q.s. |
| water | Balance |
| Total | 100.0 |

Preparation Example 4

In a similar manner to Preparation Example 3 except that the compound of Example 5 was replaced by the compounds of Example 4 and Examples 6–15, body shampoos were prepared, respectively.

The body shampoos obtained in Preparation Examples 3 and 4 each had foaming power and excellent detergency and after washing, had good touch feeling with moisturized feeling.

Preparation Example 5

The face wash having the composition as described below was prepared using the compound of the present invention. The face wash so obtained had good foaming power and detergency and after face washing, had good touch feeling with moisturized feeling.

| (Composition) | (wt. %) |
| --- | --- |
| Potassium laurate | 4.0 |
| Potassium myristate | 4.0 |
| Compound of Example 6 | 10.0 |
| Glycerin | 15.0 |
| Ethylene glycol distearate | 2.0 |
| Cationized cellulose | 0.2 |
| Water | Balance |
| Total | 100.0 |

Preparation Example 6

The face wash having the below-described composition was prepared using the compound of the present invention. The face wash so obtained had excellent foaming power and detergency and, after face washing, had good touch feeling with moisturized feeling.

| (Composition) | (wt. %) |
| --- | --- |
| Compound of Example 7 | 8.0 |
| Potassium monolaurylphosphate | 6.0 |
| Potassium laurate | 2.0 |
| Potassium myristate | 2.0 |
| Potassium stearate | 2.0 |
| Stearic acid | 4.0 |
| Octyl glucoside | 3.0 |
| 1,3-butylene glycol | 10.0 |
| Perfume | trace |
| Water | Balance |
| Total | 100.0 |

Test 2

Dish-washing detergents having the composition as shown in Table 1 were prepared and their foaming power, detergency, skin irritation and feeling upon use (hand touch feeling) were evaluated.

(Testing Method)

<Testing Method>

A porcelain dish (25 mm in diameter) was coated with 2.5 g of beef tallow to which 0.1 wt. % of Sudan III (red colorant) had been added as an indicator. The colorant was washed by rubbing at 40° C. by using a sponge soaked in 3 g of a detergent and 27 g of water (water having a hardness of 3.5° DH). The detergency and feeling upon use were evaluated by a panel consisting of 10 experts.

<Results>

As a result, the dish-washing detergent in which the compound of the present invention had been incorporated had good foaming power and excellent detergency, was free from skin irritation and had good feeling upon use.

TABLE 1

| Component | Invention Product | | |
|---|---|---|---|
| | 1 | 2 | 3 |
| Compound of Example 6 | 15 | — | — |
| Compound of Example 7 | — | 10 | — |
| Compound of Example 12 | — | — | 10 |
| Dodecyldimethylamine oxide | 3 | — | — |
| Lauryl monoethanol amide | — | 5 | — |
| Polyoxyethylene (EO8) dodecyl ether | 2 | 5 | 10 |
| Ethanol | 3 | 3 | 3 |
| Sodium m-xylene sulfonate | 2 | 2 | 2 |
| $MgSO_4 \cdot 7H_2O$ | — | 2 | — |
| Water | Balance | Balance | Balance |

Preparation Example 7

A laundry detergent composition in the powdery form having the composition as described below was prepared. The detergent so obtained had excellent detergency at low temperature (5° C.), and its detergency was not impaired even if the hardness of water employed was high (4°–8° DH).

| (Composition) | (wt. %) |
|---|---|
| Compound of Example 5, 8 or 12 | 5.0 |
| Polyoxyethylene (EO4–18) $C_6$–$C_{22}$ alkyl ether | 3.0 |
| Sodium $C_{12}$ alkylbenzene sulfonate | 20.0 |
| Sodium $C_{12}$–$C_{14}$ alkylsulfate | 5.0 |
| Sodium salt of a $C_{12}$–$C_{18}$ fatty acid | 6.0 |
| Zeolite (4A type) | 30.0 |
| Sodium carbonate | 20.0 |
| Enzyme (protease, cellulase) | 2.0 |
| Polymer (acrylic acid-maleic acid copolymer Mw = 50,000) | 3.0 |
| Fluorescent dye (DM type, Chinopearl CBS mixed type) | 0.5 |
| Perfume | 0.2 |
| Water | Balance |
| Total | 100.0 |

Preparation Example 8

A laundry detergent composition in the powdery form having the composition as described below was prepared. The detergent so obtained was excellent in finish effects for softening the clothes with good feeling.

| (Composition) | (wt. %) |
|---|---|
| Compound of Example 4 | 10.0 |
| Polyoxyethylene (EO4–18) $C_6$–$C_{22}$ alkyl ether | 25.0 |
| Cationized cellulose | 3.0 |
| Sodium salt of a $C_{12}$–$C_{14}$ fatty acid | 5.0 |
| Zeolite (4A type) | 20.0 |
| Sodium carbonate | 20.0 |
| Amorphous aluminosilicate ($Na_2O \cdot Al_2O_3 \cdot 3SiO_2$) | 10. |
| Enzyme (protease, cellulase) | 2.0 |
| Polymer (sodium polyacrylate, Mw = 50,000) | 3.0 |
| Fluorescent dye (DM type, Chinopearl CBS mixed type) | 0.5 |
| Perfume | 0.2 |
| Water | Balance |
| Total | 100.0 |

Preparation Example 9

A laundry detergent composition in the powdery form which has the composition as described below with a nonionic surfactant as a main component was prepared. The conventional detergent mainly composed of a nonionic surfactant involves problems such as low foaming power at the time of washing and inferior rinsing property, which are however overcome by the detergent having the following composition.

| (Composition) | (wt. %) |
|---|---|
| Compound of Example 5 | 5.0 |
| Polyoxyethylene (EO4–18) $C_6$–$C_{22}$ alkyl ether | 22.0 |
| Sodium salt of a $C_{12}$–$C_{14}$ fatty acid | 1.0 |
| Zeolite (4A type) | 30.0 |
| Sodium carbonate | 25.0 |
| Amorphous aluminosilicate ($Na_2O \cdot Al_2O_3 \cdot 3SiO_2$) | 10. |
| Enzyme (protease, cellulase) | 2.0 |
| Polymer (acrylic acid-maleic acid copolymer Mw = 100,000) | 3.0 |
| Fluorescent dye (DM type, Chinopearl CBS mixed type) | 0.5 |
| Perfume | 0.2 |
| Water | Balance |
| Total | 100.0 |

CAPABILITY OF EXPLOITATION IN INDUSTRY

The tris(3-aminopropyl)amine derivative, or a salt or quaternized product thereof, which is a novel compound according to the present invention, has excellent foaming power, has low skin irritation and imparts the skin or hair with favourable touch feeling. The compound according to the present invention is therefore useful as a base for hair or skin cosmetic composition, detergent, emulsifier, wetting agent, conditioning agent, modifier or the like.

We claim:

1. A tris(3-aminopropyl)amine derivative represented by the following formula (1):

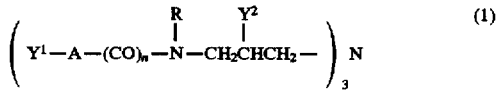

wherein R represents a linear or branched $C_{1-24}$ alkyl or alkenyl group which may be substituted by a hydroxyl group, A represents a linear or branched $C_{1-6}$ alkylene or alkenylene group which may be substituted by a hydroxyl group, a carboxyl group or a sulfonic acid group, $Y^1$ represents a carboxyl group, a sulfonic acid group or a sulfuric acid residue; and $Y^2$ represents a hydroxyl group, a sulfuric acid residue or a group —OCO—A—COOH; and n stands for 0 or 1; or a salt or quaternized product thereof, wherein at least one nitrogen atom in said quaternized product is quaternized with a $C_{1-6}$ alkyl group, a benzyl group and/or a group represented by —$(R^7O)_mH$, where $R^7$ is a $C_{2-3}$ alkylene group and m is 1 to 50, and said $C_{1-6}$ alkyl group, benzyl group and group represented by —$(R^7O)_mH$, may be optionally substituted with a hydroxyl, carboxyl or sulfonic acid group.

2. A compound according to claim 1, wherein $Y^1$ represents a sulfonic acid group or sulfuric acid residue and $Y^2$ represents a hydroxyl group or a sulfuric acid residue.

3. A compound according to claim 1, wherein $Y^1$ represents a carboxyl group and $Y^2$ represents a hydroxyl group or a —OCO—A—COOH group.

4. A compound according to claim 1, wherein R represents a linear or branched $C_{6-24}$ alkyl or alkenyl group.

5. A compound according to claim 1, which is in the form of a free base or salt.

6. An amine derivative represented by the following formula (2):

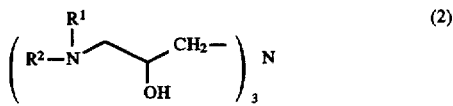

wherein $R^1$ and $R^2$ are the same or different and each independently represents a hydrogen atom or a linear or branched $C_{1-24}$ alkyl or alkenyl group, either of which may be substituted by a hydroxyl group.

7. An amine derivative according to claim 6, wherein $R^1$ represents a hydrogen atom and $R^2$ represents a linear or branched $C_{1-24}$ alkyl or alkenyl group, either of which may be substituted by a hydroxyl group.

8. An amine derivative according to claim 6, wherein $R^1$ represents a hydrogen atom and $R^2$ represents a linear or branched $C_{6-24}$ alkyl or alkenyl group.

9. A detergent composition comprising a compound according to claim 1 and a detergent base.

* * * * *